United States Patent [19]

Rogers, Jr.

[11] 4,263,456
[45] Apr. 21, 1981

[54] PROCESS OF PREPARING STYRENATED DIPHENYLAMINE

[75] Inventor: Edward A. Rogers, Jr., Barberton, Ohio

[73] Assignee: The Goodyear Tire & Rubber Company, Akron, Ohio

[21] Appl. No.: 746,650

[22] Filed: Dec. 2, 1976

[51] Int. Cl.³ .............................................. C07C 85/18
[52] U.S. Cl. .................................................... 564/315
[58] Field of Search ........................... 260/570 R, 576

[56] References Cited

U.S. PATENT DOCUMENTS

| | | | |
|---|---|---|---|
| 2,943,112 | 6/1960 | Popolf et al. | 260/576 |
| 3,452,056 | 6/1969 | Sundholm | 260/570 X |
| 3,649,690 | 3/1972 | Wheeler | 260/570 |

FOREIGN PATENT DOCUMENTS 895973  11/1953  Fed. Rep. of Germany ........... 260/570

*Primary Examiner*—Robert V. Hines
*Attorney, Agent, or Firm*—D. O. Nickey

[57] ABSTRACT

Styrenated diphenylamine is prepared by reacting styrene with diphenylamine in the presence of undried acidic clay catalyst.

2 Claims, No Drawings

PROCESS OF PREPARING STYRENATED DIPHENYLAMINE

This invention relates to the preparation of styrenated diphenylamine. More particularly it relates to the use of undried acidic clays in the preparation of para styrenated diphenylamine.

The prior art reveals the preparation of α-methyl styrenated and styrenated diphenylamines and the use of said compounds as antioxidants. Novel processes, particularly those which would produce styrenated diphenylamine of high activity, are desired.

It is an object of the present invention to provide a method for producing styrenated diphenylamine of high antioxidant activity. Other objects of this invention will become apparent as the description proceeds.

The objects of the present invention are accomplished by reacting a combination of diphenylamine and styrene in the presence of acidic clay catalyst at a temperature of from 190° C. to 220° C., preferably 200° C. to 208° C., wherein 1.95 to 2.15 mols of styrene are charged per 1 mol of diphenylamine. Preferably 2.00 to 2.05 mols of styrene are charged per 1 mol of diphenylamine.

The acidic clay used in the practice of the present invention is extremely well known in the art as Montmorillonite clay catalyst and is prepared from mineral, Montmorillonite. A major amount of the acid clay is composed of aluminum hydrosilicate. The general composition is of the type $M[(AlO_2)_x(SiO_2)_y]\cdot ZH_2O$ where M is metal cation selected from $K^+$, $Na^+$, $Ca^{+2}$, $Fe^{+2}$, $Fe^{+3}$, etc. and Z is the number of mols of water of hydration. The activity of the clay catalyst is dependent upon several factors such as the particle size, moisture content, surface area, acidity, etc.

A typical clay composition would be as follows.

| Component | Weight Percent |
| --- | --- |
| $SiO_2$ | 70–75 |
| $Al_2O_3$ | 15–20 |
| $Fe_2O_3$ | |
| MgO | |
| GaO | 8–15 |
| $K_2O$ | |

Examples of these catalysts are the activated Montmorillonite catalyst of the K series producted by Chemetron Corporation, and activated clay adsorbents of Filtrol Corporation. The catalysts should not be dried and should contain 6 to 9 percent water, preferably 7 to 8 percent water. The water content of the catalyst is calculated as the water of hydration plus free water.

The reaction products of the present invention are a mixture of styrenated diphenylamines.

The reaction may be accomplished batchwise or on a continuous basis for various pressures, including atmospheric pressure. The product is an effective antioxidant which can be used in the stabilization of materials subject to oxidation degradation, high density foam rubbers and diene rubbers such as butadiene/nitrile rubbers.

In a typical operation styrene is added slowly to a hot mixture of diphenylamine and the catalyst at the desired reaction temperature.

The amount of catalyst will vary depending upon the particular catalyst used. As a guideline, but not a limitation, 8 to 16 parts by weight of catalyst can be used per 100 parts by weight of diphenylamine.

The following example illustrates but does not limit the practice of the present invention.

EXAMPLE 1

Molten diphenylamine (150 pounds) and Montmorillonite clay from Girdler: KSF (15 pounds) are heated to 204° C. with the reaction vented. The reactor is then sealed and styrene (189.5 pounds) is added over a 25 to 45 minute period. The batch is then stirred for 1 hour at 204° C. and then filtered. Product analysis showed diphenylamine (DPA) 0.5 percent, o-monostyryl DPA (4.4 percent), p-styryl DPA (7.5 percent), O-o distyryl DPA (9.2 percent), o-p distyryl DPA (11.7 percent), p-p distyryl DPA (37.4 percent) and tristyryl DPA (27.0 percent). The undried KSF water content was 8 percent.

While certain representative embodiments and details have been shown for the purpose of illustrating the invention it will be apparent to those skilled in this art that various changes and modifications may be made therein without departing from the spirit or scope of the invention.

What I claim is:

1. In a process for the preparation of styrenated diphenylamine comprising reacting a combination comprising (a) diphenylamine and (b) styrene in the presence of a catalytic amount of an undried acid clay catalyst containing a major amount of aluminum hydrosilicate at a reaction temperature of from 190° to 220° C. wherein the level of styrene is from 1.95 to 2.15 mols per mol of diphenylamine, the improvement characterized in that the undried acid clay catalyst contains 6 to 9 percent water.

2. A process according to claim 1 wherein the reaction temperature is from 200° C. to 208° C. and the level of styrene is from 2.00 to 2.05 mols per mol of diphenylamine.

* * * * *